(12) United States Patent
Ushiyama

(10) Patent No.: US 6,265,203 B1
(45) Date of Patent: Jul. 24, 2001

(54) MICROORGANISM CULTURE MATERIAL CONTAINING A WATER-SOLUBLE POLYMER LAYER AND A POROUS MATRIX LAYER

(75) Inventor: Masashi Ushiyama, Yokohama (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/106,174

(22) Filed: Jun. 29, 1998

Related U.S. Application Data

(63) Continuation of application No. PCT/JP96/03816, filed on Dec. 26, 1996.

(30) Foreign Application Priority Data

Dec. 27, 1995 (JP) .................................................. 7-353701
Jan. 26, 1996 (JP) .................................................. 8-032900
Jul. 16, 1996 (JP) .................................................. 8-205379

(51) Int. Cl.⁷ ............................... C12N 1/20; C12N 1/14; C12N 1/16; C12N 1/18; C12Q 1/02
(52) U.S. Cl. ......................... 435/253.6; 435/29; 435/34; 435/243; 435/255.21; 435/255.7; 435/256.8; 435/805
(58) Field of Search ................................ 435/243, 252.1, 435/253.6, 255.21, 255.7, 256.8, 805, 29, 34

(56) References Cited

U.S. PATENT DOCUMENTS 3,881,993    5/1975  Freake et al. ...................... 435/287.7

FOREIGN PATENT DOCUMENTS

| | | |
|---|---|---|
| 54-132292 | 10/1979 | (JP) . |
| 63-46096 | 9/1988 | (JP) . |
| 2-49705 | 10/1990 | (JP) . |
| 2-61976 | 12/1990 | (JP) . |
| 3-15379 | 1/1991 | (JP) . |
| 4-117299 | 4/1992 | (JP) . |
| 5-505522 | 8/1993 | (JP) . |
| 6-181745 | 7/1994 | (JP) . |
| 6-311880 | 11/1994 | (JP) . |
| 7-501943 | 3/1995 | (JP) . |
| 7-289285 | 11/1995 | (JP) . |

OTHER PUBLICATIONS

Kogyo Zairyo (Industrial Mat.).
Kino Zairyo (Functional Mat.), Vo. 13, No. 5, p43–50 "High Water–Absorptive Polymer".

*Primary Examiner*—David M. Naff
(74) *Attorney, Agent, or Firm*—McDermott, Will & Emery

(57) ABSTRACT

A culture material is formed containing a water-soluble polymer layer and a porous matrix layer arranged such that when water is applied to the surface of the matrix layer the water diffuses through the matrix layer to dissolve the water-soluble polymer layer which then gradually penetrates into the matrix layer to form a single layer for use as a culture medium on which a microorganism can be grown to form colonies. The water-soluble polymer layer or water added to the matrix layer can contain nutrients for the microorganism, and the microorganism can be added with the water. The culture material has a water content of not more than 50%, and is sufficiently insoluble in water such that it substantially holds its original shape for at least 30 minutes when in contact with water having a temperature of not more than 50° C. The culture medium produced by adding water to the culture material may be used for quantitative or semi-quantitative determination of microorganisms that may be present in a sample such as obtained from food.

18 Claims, 8 Drawing Sheets

MICROORGANISM CULTURE MATERIAL CONTAINING A WATER-SOLUBLE POLYMER LAYER AND A POROUS MATRIX LAYER

REFERENCE TO RELATED APPLICATION

This Application is a continuation of International Application No. PCT/JP96/03816, whose international filing date is Dec. 26, 1996, which in turn claims the benefit of Japanese Application No. 353701/1995, filed Dec. 27, 1995, Japanese Application No. 32900/1996, filed Jan. 26, 1996 and Japanese Application No. 205379/1996, filed Jul. 16, 1996, the disclosures of which Applications are incorporated by reference herein. The benefit of the filing and priority dates of the International and Japanese Applications is respectfully requested.

TECHNICAL FIELD

The present invention relates to a culture medium for easily culturing and detecting microorganisms present in, for instance, foods and environment as well as culture materials used in the culture medium. The culture medium is converted into a medium in which microorganisms can grow, by the addition of water.

BACKGROUND ART

If a conventional method for culturing microorganisms is explained while taking the determination of the total viable count in the food test by way of example, dehydrated agar medium is first dissolved and sterilized and then maintained at a temperature of about 45° C. A predetermined amount of the agar medium is dispensed in, for instance, sterilized Petri dishes to which a constant amount of a sample such as a suspension of a food is previously added, followed by pour culture thereof, solidification of the agar, culturing at a constant temperature and counting the number of developed colonies of microorganisms. Thus, the conventional method for culturing microorganisms requires much time and labor since, in the method, a culture medium must preliminarily be prepared, sterilized and then maintained at a temperature at which the medium is not solidified. In addition, the method in general uses a large number of plastic Petri dishes and therefore, generates a large amount of plastic waste. To easily and rapidly carry out bacteriological tests, it is preferred to develop a method which permits the omission of the preparation of such a culture medium which requires much time and labor and is accompanied by the generation of a lesser amount of plastic waste.

Moreover, an environmental test in general comprises the steps of wiping a predetermined area of a subject to be tested with, for instance, a swab; dipping the swab with sterilized water or physiological saline so that the bacterial cells adhered to the swab are suspended in the sterilized water or physiological saline; inoculating an agar medium preliminarily prepared with the suspension or culturing the bacterial cells according to the pour plate method similar to that used above; and then testing the bacterial cells and determining the viable counts.

There have already been put on the market several types of simplified culture media which are designed such that it is easy to handle and is fit for various purposes. These commercially available simplified culture media may be classified for convenience into, for instance, stamp type one (Japanese Un-Examined Patent Publication (hereinafter referred to as "J. P. KOKAI") No. Hei 4-117299); filter-type and film-type ones (Japanese Examined Patent Publication (hereinafter referred to as "J. P. KOKOKU") No. Hei 2-49705 and J. P. KOKAI No. Hei 3-15379); and test paper-type one.

When using the stamp-type culture medium, the bacteriological test is carried out by dispensing an agar medium in plastic containers to such an extent that the medium stands up above the rim of the container, directly bringing the surface of the agar medium into contact with a subject to be tested to thus inoculate the medium with microorganisms and culturing the microorganisms. This culture medium may easily be used for briefly testing the contamination of environment with microorganisms, but this test is insufficient in quantitativeness because of a small area size of the medium and it is difficult to test a subject having a curved and/or uneven surface using the medium. Moreover, the method also suffers from a problem in that the culture medium is directly brought into contact with a subject to be tested and therefore, the method is not used for the test of, for instance, foods. In addition, the method uses plastic Petri dishes and therefore, generates a large amount of plastic waste after the culturing, like the foregoing conventional method. The filter-type culture medium is suitable for the test of liquid samples, but is not easily used for the test of samples other than liquids. The test paper-type culture medium suffers from a problem in that it does not permit any quantitative analysis. The film-type culture medium can easily be applied to the food test since the medium permits a quantitative analysis, but when it is used for the environmental test, the medium cannot directly come in contact with a subject to be tested unlike the stamp-type one.

As has been discussed above, there have been proposed several types of commercially available simplified culture media, but none of them have presently been able to be used, alone, in various applications such as food tests, tests of liquid samples, tests in which the medium directly comes in contact with a subject to be tested.

SUMMARY OF THE INVENTION

An object of the present invention is to provide a culture medium for easily culturing and detecting microorganisms in, for instance, foods and environment as well as materials used in the culture medium.

Another object of the present invention is to provide a simplified culture medium which can be used in wide variety of applications such as food tests, tests of liquid samples, tests in which the medium directly comes in contact with a subject to be tested as well as materials used in the culture medium.

A further object of the present invention is to provide a culture medium which permits quantitative or semi-quantitative determination of microorganisms present in foods or environment using food suspensions or suspensions prepared by swabbing a sample to be tested and then dispersing the sample in a solvent, as well as materials used in the culture medium.

A still further object of the present invention is to provide a culture medium which permits quantitative or semi-quantitative determination of microorganisms present in samples to be tested by adding sterilized water to thus humidify the medium and then bringing the humidified medium into direct contact with a subject to be tested as well as materials used in the culture medium.

According to the present invention, there is thus provided a material for culturing microorganisms (microorganism culture material) having a water-retention ability and a water content of not more than 50% by weight and is insoluble in water of not more than 50° C. as well as a culture medium obtained using the material.

BRIEF DESCRIPTION OF THE DRAWINGS

In FIGS. 1 to 3, the reference numeral 1 represents a substrate; 2 a water-absorptive layer; 3 colonies of microorganisms; 4 a water-soluble polymer layer; and 5 a porous matrix layer.

DETAILED DESCRIPTION OF THE INVENTION

Figure 1:
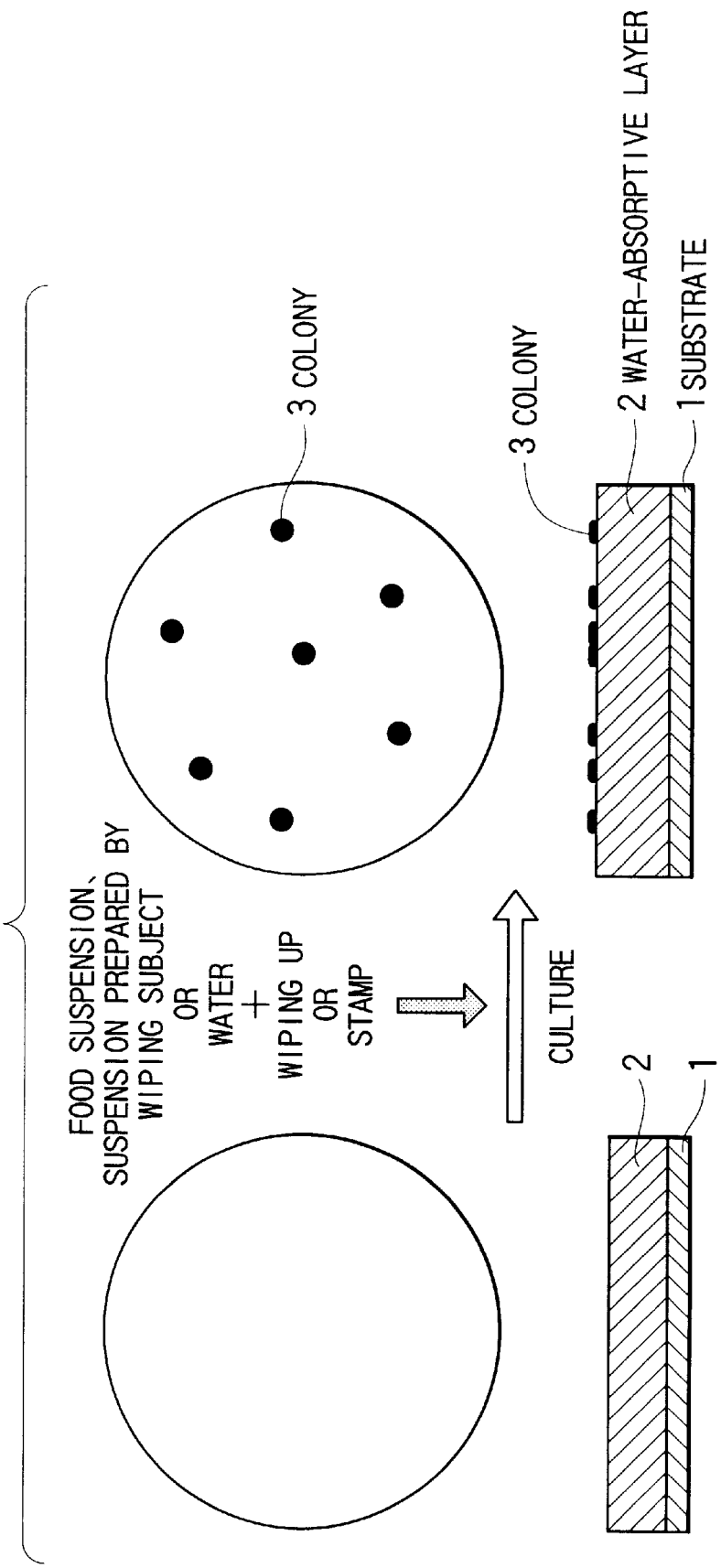
FIG. 1 is a diagram showing plane and cross sectional views of a specific example according to a first embodiment of the present invention as well as a mode of application thereof.

The microorganism culture material of the present invention has a water-retention ability, a water content of not more than 50% by weight and is substantially insoluble in water having a temperature of not more than 50° C. In this regard, the term "has a water-retention ability" used herein means that when water (containing nutrients) is added to the material in an amount of 0.2 to 1.5 ml per 10 cm$^2$ of the latter, the material can retain water to such an extent that a motile microorganism cannot move on the surface of the material through migration and cannot penetrate into the internal layer thereof at the optimum growth temperature within 5 hours and one microorganism forms a single colony on the surface of the culture material. In other words, the moisture is retained by the ingredients of the culture material or serves to form a highly viscous solution before the motile microorganism initiates the cell division and thus there is not any water in which the microorganism can move. The culture material suppresses or prevents any movement of motile microorganisms on the surface of the material and any penetration of the microorganisms into the interior thereof because of such an ability of water retention and accordingly, the microorganisms distributed on the surface of the culture material when a sample is applied thereto can form colonies mainly on the surface thereof.

In addition, the term "substantially insoluble in water having a temperature of not more than 50° C." means that when water having a temperature of not more than 50° C. is added to the material or water is added thereto and maintained at not more than 50° C., the culture material can almost hold its original shape over at least 30 minutes. For instance, when the culture material may be defined to be one "substantially insoluble in water of not more than 50° C." so far as it can almost hold its original shape even when the ingredients (for instance, water-absorbing materials and water-soluble polymers as will be discussed below) for the culture material gets swollen through absorption of water or is dissolved therein. Moreover, when a culture material comprises a water-absorbing material and water is applied onto the surface of the material, the water is absorbed by the water-absorbing material (or optionally the latter gets swollen) and the thickness of the culture material increases through absorption of water, but the original shape of the material may approximately be maintained. Furthermore, as will be detailed below, when water is applied to a culture material which comprises a porous matrix layer and a water-soluble polymer layer, through the porous matrix layer, the water horizontally and vertically diffuses through the porous matrix layer and arrives at the water-soluble polymer layer to thus dissolve the polymer, the resulting water-soluble polymer solution in turn enters into the matrix layer and thus these layers are apparently united. At this stage, the original shape of the porous matrix layer may approximately be maintained. Such a culture material can likewise be defined to be one "substantially insoluble in water of not more than 50° C.".

The present invention is excellent in operating characteristics and thus can be used in, for instance, the test wherein a subject is directly wiped by the culture material.

The culture material of the present invention has a moisture content of not more than 50% by weight. This limit is determined while taking into consideration the storability of the material and the moisture content is preferably not more than 40% by weight, more preferably not more than 30% by weight. The moisture content is preferably as low as possible, but the lower limit thereof may vary depending on the ingredients and the selected method for storing the culture material.

According to a first embodiment of the present invention, there is provided a microorganism culture material comprising a sheet-like material which is water-absorptive (or water-swellable) and insoluble in water and which can substantially maintain its shape even when it absorbs water or gets swollen with water.

According to a second embodiment of the present invention, there is provided a microorganism culture material comprising a water-soluble polymer layer and a porous matrix layer.

The present invention will further be described below.
Water-Absorptive Materials As a sheet-like material (hereinafter referred to as "water-absorptive material"), which is water-absorptive (or water-swellable) and insoluble in water and which can substantially maintain its original shape even when it absorbs water or gets swollen with water, the following materials may be used in the present invention:
(1) Crosslinked Products of Water-Soluble Polymers
(2) Water-Absorptive Polymer Derived from Starch
(3) Cellulosic Water-Absorptive Polymers
(4) Acrylic Water-Absorptive Polymers
(5) Maleic Anhydride Unit-Containing Copolymers
(6) Vinyl Pyrrolidone Unit-Containing Copolymers
(7) Polyethereal Water-Absorptive Polymers (such as polyethylene glycol-diacrylate crosslinked polymer)

(8) Hydrolyzates of Acrylic Fibers
(9) Other Water-Absorptive Polymers

All of these materials are known and they are detailed in, for instance, "KINO ZAIRYO (Functional Materials)", Vol. 13, No. 5, pp. 43–50 (May, 1993); KOGYO ZAIRYO (Industrial Materials)", Vol. 42, No. 4, pp. 18–52 (April, 1994); and MASUDA Fusayoshi, "High Water-Absorptive Polymer", edited by KOBUNSHI GAKKAI (Polymer Society of Japan), issued by Kyoritsu Publishing Co., Ltd.

As the water-soluble polymers used for preparing the crosslinked derivatives thereof (1), there may be listed, for instance, polyvinyl alcohols (PVA) (preferably those having a molecular weight ranging from 5,000 to 200,000 and a degree of saponification ranging from 75 to 99%); modified PVA's (those obtained by polymerizing vinyl acetate in the presence of an unsaturated dicarboxylic acid [such as maleic acid, fumaric acid, glutaconic acid, allyl malonic acid, anhydrides thereof or monoalkyl esters thereof](regarding the polymerization methods, see, for instance, J. P. KOKOKU No. Sho 61-42002), those obtained by reacting PVA's with cyclic acid anhydrides, and those obtained by modifying PVA's with basic substituents (such as "Gosefimer C series", "Gosefimer F series" and "Gosefimer L series" available from The Nippon Synthetic Chemical Industry Co., Ltd.); cellulose derivatives [such as carboxymethyl cellulose (CMC), hydroxyalkyl cellulose (e.g., hydroxymethyl cellulose)]; starch and derivatives thereof [such as soluble starch, carboxymethyl derivative of starch]; polysaccharides other than cellulose derivatives, starch and derivatives thereof [such as hyaluronic acid, guar-gum, gum arabic]; acrylic acid and derivatives thereof [such as polyacrylic acid, polyacrylic acid salts, acrylic acid (salt)-vinyl alcohol copolymers]; polyethers [such as polyethylene glycol, polypropylene glycol]; and proteins [such as collagen].

Examples of crosslinking agents for preparing the foregoing crosslinked products of water-soluble polymers are dialdehydes such as glyoxal; methylol compounds such a s trimethylolmelanin; epoxy compounds such as epichlorohydrin; diisocyanates such as diphenylmethane isocyanate; metal salts of organic acids; metal alkoxides; carboxylic acid anhydride such as tetrahydrofuran tetracarboxylic acid anhydride; borane; boric acid; phosphorous atom-containing compounds; and photo-crosslinking a gents.

Examples of the water-absorptive polymer (2) derived from starch are hydrolyzates of starch-acrylonitrile graft copolymers; starch-acrylic acid graft copolymers; starch-styrenesulfonic acid graft copolymers; starch-vinyalsulfonic acid graft copolymers; and starch-acrylamide graft copolymers.

Examples of the cellulosic water-absorptive polymers (3) include cellulose-acrylonitrile graft copolymers; cellulose-styrenesulfonic acid graft copolymers; and crosslinked products of carboxymethyl cellulose.

Examples of the acrylic water-absorptive polymers (4) include sodium acrylate-vinyl alcohol copolymers (saponified products of methyl acrylate-vinyl acetate copolymers); saponified products of polyacrylonitrile type copolymers; hydroxyalkyl (such as hydroxymethyl, hydroxyethyl) methacrylate polymers.

These polymers may be used alone or in combination of at least two of them.

Water-Soluble Polymers

As water-soluble polymers for forming the water-soluble polymer layer used in the present invention, there may be listed, for instance, PVA's (preferably those having a molecular weight ranging from 30,000 to 200,000 and a degree of saponification ranging from 75 to 90%); modified PVA's (those obtained by polymerizing vinyl acetate in the presence of an unsaturated dicarboxylic acid [such as maleic acid, fumaric acid, glutaconic acid, allyl malonic acid, anhydrides thereof or monoalkyl esters thereof](regarding the polymerization methods, see, for instance, J. P. KOKOKU No. Sho 61-42002), those obtained by reacting PVA's with cyclic acid anhydrides, and those obtained by modifying PVA's with basic substituents (such as "Gosefimer C series", "Gosefimer F series" and "Gosefimer L series" available from The Nippon Synthetic Chemical Industry Co., Ltd.)); cellulose derivatives [such as carboxymethyl cellulose (CMC), hydroxyalkyl cellulose (e.g., hydroxymethyl cellulose)]; starch and derivatives thereof [such as soluble starch, carboxymethyl derivative of starch]; polysaccharides other than cellulose derivatives, starch and derivatives thereof [such as hyaluronic acid, guar-gum, gum arabic]; acrylic acid and derivatives thereof [such as polyacrylic acid, polyacrylic acid salts, acrylic acid (salt)-vinyl alcohol copolymers]; polyethers [such as polyethylene glycol, polypropylene glycol]; and proteins [such as collagen].

The water-soluble polymer for forming the water-soluble polymer layer has a viscosity, as determined using a 4% by weight aqueous solution at 20° C. and measured using an Ostwald viscometer, preferably not less than 10 cps and more preferably 15 to 80 cps. The use of such a water-soluble polymer is preferred since it permits the inhibition of any penetration of microorganism into the interior of the culture medium and prevent any movement of the microorganism, which initiates cell-division, on the surface of the medium, thus induces the formation of colonies principally on the surface thereof and accordingly makes the counting up of the colonies easy.

Porous Matrix Layer-Forming Materials

As materials for forming the porous matrix layer used in the present invention, there may be mentioned, for instance, textile fabrics and nonwoven fabrics formed from, for instance, synthetic fibers [such as fibers of nylons, polyesters (in particular, those subjected to a hydrophilization treatment), polyacrylonitrile, polyolefins (in particular, those subjected to a hydrophilization treatment) and polyurethanes], semi-synthetic fibers (such as rayon fibers), natural fibers [such as fibers of cellulose, cotton, silk and wool (animal hair)] and inorganic fibers (such as glass fibers); porous films and sponges produced from the ingredients of the foregoing fibers; and porous ceramics. The average diameter of these fibers is preferably not more than 30 $\mu$m, more preferably not more than 15 $\mu$m and most preferably not more than 10 $\mu$m.

Microorganism-Culture materials

The microorganism culture materials according to the present invention comprises a single ingredient or a plurality of ingredients which are mixed or compounded together.

The culture material comprising a single ingredient can easily be prepared by, for instance, applying a suspension which is obtained by dispersing an ingredient (a water-absorptive polymer) in a solvent, onto an appropriate substrate (such as a polyester film) and then evaporating the solvent. In the preparation of the culture material, nutrients may be incorporated into the coating liquid to give a nutrient-containing culture material. Alternatively, the culture material may likewise be prepared by mixing a water-absorptive polymer and a water-soluble polymer and then forming the mixture into a sheet or a film; by crosslinking an appropriate sheet or film with a water-soluble polymer; by crosslinking an appropriate fiber material with a water-soluble polymer and then forming into a sheet; or by forming a water-soluble polymer into fibers and then forming the fibers into a sheet.

A composite may be prepared by, for instance, a method which comprises mixing the ingredient of the foregoing water-soluble polymer layer (a film- or sheet-like product) with that of the porous matrix layer (such as fibers) and then forming the resulting mixture into a film or sheet; a method which comprises impregnating, with a solution of the ingredient of the foregoing water-soluble polymer layer, fibers or processed fiber articles such as nonwoven fabric or textile fabrics as the ingredients of the porous matrix layer and then drying the same; a method which comprises overlaying fibers or a processed fiber article as the ingredient of the porous matrix layer on a solution of the ingredient for the foregoing water-soluble polymer layer and then drying; or a method which comprises adhering fibers or a processed fiber article as the ingredient of the porous matrix layer to a film or sheet prepared from the ingredient for the foregoing water-soluble polymer layer. In particular, if the microorganism culture material is prepared by laminating a fiber-processed article with a film or sheet prepared from the ingredient for the foregoing water-soluble polymer layer, the resulting culture material shows high strength and the use thereof as a culture medium permits the improvement of the operability upon the test of a subject which includes the direct contact between the culture material and the subject as a sampling step (hereinafter referred to as "direct contact test").

The thickness of the microorganism culture material of the present invention prior to the addition of water is not particularly restricted, but is preferably not more than 4 mm and more preferably not more than 3 mm while taking into consideration reduction of space and easiness of counting the number of colonies. In addition, the thickness varies depending on the adsorption of each specific culture material for water, but is preferably not less than 10 $\mu$m from the practical standpoint.

The culture material of the present invention is converted into the culture medium according to the present invention by incorporating nutrients into the material and the medium is converted into one, which can be used in the culturing of microorganisms by adding water to the medium in an amount required for the growth of the microorganisms. In general, the microorganism culture material and the culture medium of the present invention are preferably in the form of a plate. The plate may have any shape such as circular, elliptic, trapezoidal, square, rectangular, triangular and other polygonal shapes, but preferred are, for instance, circular and square shapes from the viewpoint of its production and use. Moreover, the area size of the portion of the plate-like culture material which is directly brought into contact with a subject preferably ranges from 1000 to 6500 $mm^2$ and more preferably 1500 to 3000 $mm^2$ Shown in FIG. 1 are a plane view and a cross sectional view of a specific example according to a first embodiment of the present invention as well as a mode of the use thereof. In this specific example, a water-absorptive layer 2 containing nutrients is disposed on a substrate 1. Microorganisms are applied to the surface of the water-absorptive layer 2 by dropwise addition of a sample to be tested to the surface of the layer 2; or by directly wiping up a sample to be tested with the surface of the layer 2, followed by culturing of the microorganisms. Water may penetrate into the interior of the water-absorptive layer 2, but microorganisms cannot penetrate into the layer 2 and remain on the surface of the layer on which they grow while taking the nutrients included in the water-absorptive layer to thus form colonies 3.

The average thickness of the water-absorptive layer 2 suitably ranges from about 0.01 to 4 mm, preferably not more than 3 mm and more preferably 0.05 to 2.0 mm.

The substrate 1 may be used or may be omitted and if it is used, the thickness thereof suitably ranges from about 0.03 to 2 mm, preferably not more than 1 mm and more preferably 0.04 to 0.2 mm.

Figure 2:
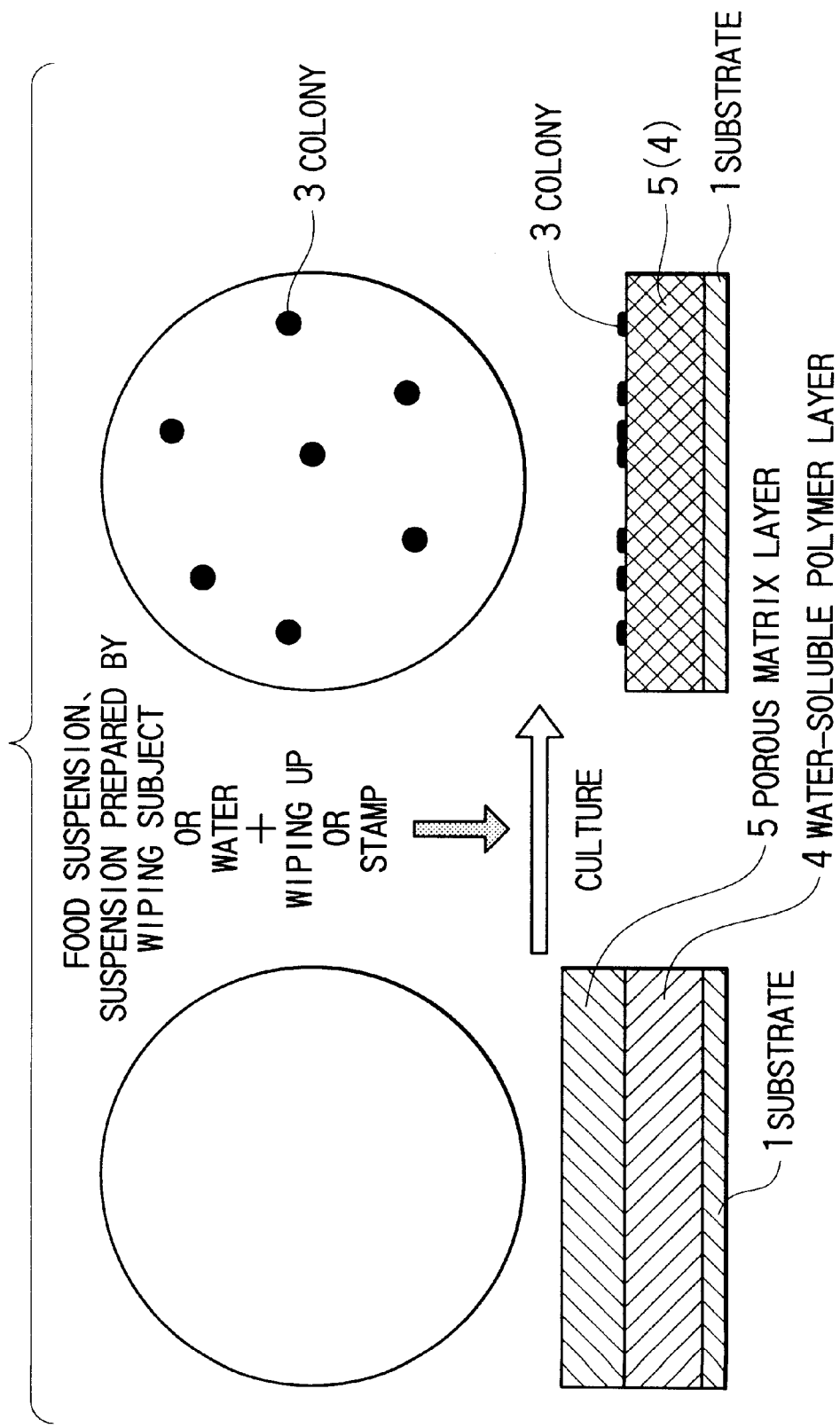
FIG. 2 is a diagram showing plane and cross sectional views of a specific example according to a second embodiment of the present invention as well as a mode of application thereof.

Shown in FIG. 2 are a plane view and a cross sectional view of a specific example according to a second embodiment of the present invention as well as a mode of the use thereof. In this specific example, the culture material comprises a nutrient-containing water-soluble polymer layer 4 and a porous matrix layer 5, which are laminated with a substrate 1. Microorganisms are applied to the surface of the porous matrix layer 5 by dropwise addition of a sample to be tested to the surface of the layer 5 or by directly wiping up the sample with the surface of the layer 5 or by directly bringing the surface of the layer 5 into contact with the sample, followed by culturing of the microorganisms. Water may horizontally and vertically diffuse in the interior of the porous matrix layer 5, then arrives at the water-soluble polymer layer 4 at which it dissolves the polymer layer 4 and the nutrients. The water-soluble polymer and the nutrients dissolved in the water gradually penetrate into the matrix layer 5 and thus the water-soluble polymer solution and the porous matrix layer 5 are apparently united together. At this stage, the microorganisms applied to the surface of the porous matrix layer 5 partially migrate into the matrix layer 5 along with the moisture, but cannot penetrate into the water-soluble polymer layer. For this reason, when the upper end of the water-soluble polymer solution arrives at the surface of the matrix layer 5, the microorganisms grow on the surface of the matrix layer 5 to thus form colonies 3.

In the microorganism culture material according to the second embodiment of the present invention, the average thickness of the water-soluble polymer layer 4 suitably ranges from about 0.01 m to 3 mm, preferably 0.05 to 2.5 mm and more preferably 0.1 to 2.0 mm, while that of the porous matrix layer 5 suitably ranges from about 0.2 to 4 mm, preferably 0.3 to 3 mm and more preferably 0.4 to 2.5 mm. The average thickness of the microorganism culture material which comprises a water-soluble polymer layer 4 and a porous matrix layer 5 suitably ranges from about 0.2 to 4 mm, preferably 0.3 to 3 mm and more preferably 0.6 to 2.5 mm.

The substrate 1 may be used or may be omitted and if it is used, the thickness thereof suitably ranges from about 0.03 to 2 mm, preferably not more than 1 mm and more preferably 0.04 to 0.2 mm.

The amount of water retained by the porous matrix layer 5 of the microorganism culture material of the invention is preferably not less than 15 $mg/cm^2$, more preferably 20 to 200 $mg/cm^2$ and most preferably 30 to 100 $mg/cm^2$. In addition, the weight of the porous matrix layer 5 per unit area preferably ranges from 10 to 200 $g/m^2$, more preferably 30 to 150 $g/m^2$ and the density of the matrix layer 5 preferably ranges from 3 to 600 $kg/m^3$ and more preferably 12 to 250 $kg/m^3$.

The weight of the water-soluble polymer layer 4 of the microorganism culture material of the invention per unit area thereof is preferably not less than 0.5 time, more preferably 0.5 to 4 times and most preferably 0.5 to 2 times the weight of the porous matrix layer 5 per unit area.

Figure 3:
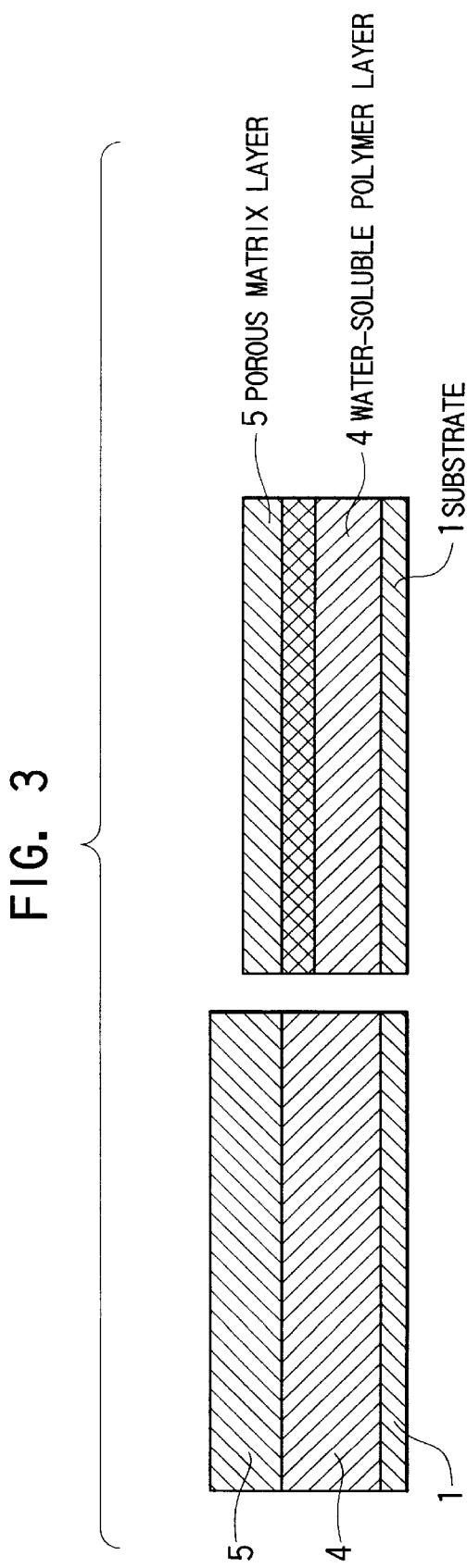
FIG. 3 is a diagram showing another specific example according to the second embodiment of the present invention.

In the second embodiment of the present invention, the porous matrix layer 5 may partially or completely penetrate into the water-soluble polymer layer 4, as will be seen from FIG. 3. In general, the overlap between the polymer layer 4 and the matrix layer 5 is suitably not more than 90% of the thickness of the matrix layer.

Substrate (Reinforcing Layer) or Reinforcing Material

The microorganism culture material of the present invention may further comprise a substrate (reinforcing layer) or a reinforcing material. As materials for such substrates (reinforcing layers) or reinforcing materials, suitably used are, for instance, sheets or films produced from water-insoluble synthetic resins (such as polyesters, nylons and polyolefins). It is suitable that the thickness of the substrate (or reinforcing layer) preferably ranges from about 0.03 to 2 mm and more preferably 0.04 to 0.2 mm. In the second embodiment, the substrate 1 (or reinforcing layer) is preferably formed on the side of the water-soluble polymer layer 4 opposed to the side to which the porous matrix layer 5 is fitted, as shown in FIG. 2.

The reinforcing material may be fitted to the culture material by combining solid body formed from the foregoing material with the microorganism culture material through, for instance, adhesion, adsorption or attachment. In addition, a solid material, as a reinforcing layer, may be applied to a culture medium for growing microorganisms (hereinafter also referred to as "microorganism culture medium") produced through, for instance, adhesion, adsorption or attachment to thus give a reinforced microorganism culture medium. Alternatively, a reinforced microorganism culture material or culture medium can likewise be produced by mixing at least one ingredient for the culture material (water-absorptive materials, water-soluble polymers and materials for the porous matrix layer) with a reinforcing material and then molding the resulting mixture.

The microorganism culture material or culture medium of the present invention may be provided with a protective cover such as a film of, for instance, a plastic material.

Microorganism Culture Medium

The microorganism culture medium of the present invention may be prepared by incorporating at least one nutrient into the microorganism culture material of the present invention. The moisture content of the microorganism culture material and medium of the present invention is not more than 50% by weight, but preferably as low as possible from the viewpoint of the storage stability. For instance, the moisture content is preferably not more than 30% by weight.

The microorganism culture material of the invention may be converted into a culture medium which permits the growth of microorganisms by addition of moisture and nutrients. In addition, the microorganism culture medium of the invention is a dry culture medium and can thus be converted into a culture medium capable of growing microorganisms by addition of moisture.

The microorganism culture medium of the invention is prepared by incorporating nutrients required for the growth of microorganisms into the foregoing microorganism culture material through impregnation, attachment or adsorption and then drying the material. Alternatively, a culture material may also be prepared using a product obtained by mixing at least one ingredient for the microorganism culture material (water-absorptive materials, water-soluble polymers and materials for the porous matrix layer) with nutrients, then forming the resulting mixture into a desired shape (such as film-, sheet-, fiber- and textile fabric-like shapes).

When a sample liquid is added to a microorganism culture material or a microorganism culture medium, which comprises a porous matrix layer and a water-soluble polymer layer, the sample liquid may be applied thereto from either side thereof, but it is preferred to apply the sample from the porous matrix layer side. In this case, the sample liquid diffuses in the porous matrix layer in the horizontal direction and simultaneously diffuses in the vertical direction, then arrives at the water-soluble polymer layer in which the polymer is dissolved and the resulting polymer solution enters into the matrix layer. The viscosity of the polymer solution is high and accordingly, the solution effectively inhibits any migration of microorganisms (movement thereof into the solution). When the water-soluble polymer layer includes nutrients, the nutrients are released from the polymer layer and thus, microorganisms start to grow and initiate cell-division.

The microorganisms present in the sample liquid are distributed throughout the entire surface of the porous matrix layer when they are applied to a microorganism culture material or a microorganism culture medium, but do not penetrate in the interior of the polymer layer since the water-soluble polymer is gradually dissolved. The microorganisms are pushed up to the surface of the porous matrix layer during the process in which the water-soluble polymer layer is gradually dissolved and united with the porous matrix layer (see FIG. 2), colonies are thus formed on the surface of the matrix layer and this makes the count of the number of colonies easy. Since the colonies are formed on the surface of the matrix layer, the microorganism culture material or medium does not suffer from a problem associated with the culture medium using filter paper in which colonies are formed within the filter paper and this makes the count of the microorganism impossible or inaccurate.

Nutrients of Culture Medium

Nutrients used in the culture medium of the present invention are not restricted to any specific ones so far as they are adapted for microorganisms to be cultured. There may be used, for instance, the liquid media usually used and the culture medium components obtained by removing agar from the agar culture media.

Examples of nutrients are yeast extract-peptone-dextrose mixtures, meat extract-peptone mixtures, peptone-soybean peptone-dextrose mixtures and those obtained by adding dipotassium hydrogenphosphate and/or sodium chloride to the foregoing nutrients, for total viable counts; nutrient mixtures in which $E.$ $coli$ and coliforms can grow such as sodium deoxycholate-peptone-ammonium iron citrate-sodium chloride-dipotassium hydrogenphosphate-lactose-Neutral Red mixtures, peptone-lactose-dipotassium hydrogenphosphate-Eosine Y-Methylene Blue mixtures, and peptone-lactose-sodium chloride-bile salts mixtures and potassium hydrogenphosphate-tryptophane mixtures to which fluorescent and/or chromophoric substrates such as β-glucuronidase and/or β-galactosidase are added, for tests of $E.$ $coli$ and coliforms; meat extract-peptone-sodium chloride-mannitol-Phenol Red-yolk mixtures, peptone-meat extract-yeast extract-sodium pyruvate-glycine-lithium chloride-yolk tellurite solution mixtures, for Staphylococcus-test; yeast extract-peptone-sucrose-sodium thiosulfate-sodium citrate-sodium cholate-ferric citrate-sodium chloride-bovine bile-Bromothymol Blue-Thymol Blue mixtures for Vibrio-test; bovine brain extract-heart extract-peptone-dextrose-dipotassium hydrogenphosphate-sodium azide-Bromothymol Blue-2,3,5-triphenyl tetrazolium chloride mixtures for Enterococcus-test; and peptone-dextrose mixtures and potato extract-dextrose mixtures, for yeasts and moulds-test.

The culture medium may further comprise, for instance, dyes for making the observation of colonies formed easier, a chromophoric or fluorescent substrate for an enzyme in order to detect a specific microorganism, or substances capable of inhibiting any growth of microorganisms other than a specific microorganism to be detected.

The microorganism culture medium can likewise be prepared by impregnating a microorganism culture material free of any nutrient with nutrients or adding nutrients to the culture material.

Alternatively, the microorganism culture material of the present invention can be used as a culture medium after the addition of water containing nutrients thereto.

Method of Using Microorganism Culture Medium

The microorganism culture medium of the invention can be used as follows.

A suspension obtained by treating a food or the like in, for instance, a homogenizer or a swabbing suspension (an aqueous dispersion obtained by swabbing) is added to the microorganism culture medium of the invention after appropriate dilution. The microorganisms are cultured while taking measures to prevent any evaporation of moisture, for instance, accommodation of the culture medium in a bag or a Petri dish or sandwiching of the culture medium between plastic films.

In addition, when the test includes a step of directly bringing the medium into contact with the subject to be tested (hereinafter also referred to as "direct contact-test"), the microorganism culture medium is moistened by addition of sterilized water and then directly brought into contact with the subject. Thereafter, the microorganisms are cultured while taking measures to prevent any evaporation of water, for instance, accommodation of the culture medium in a bag or a Petri dish or sandwiching of the culture medium between plastic films.

When microorganisms are cultured while sandwiching the microorganism culture medium between, for instance, plastic films, the medium may previously be attached or adhered to one of the films.

The microorganism culture medium of the invention permits the direct contact-test in addition to the usual food test and environmental test.

EXAMPLES

The present invention will hereinafter be described in more detail with reference to the following Examples, but the present invention is not limited to these specific Examples at all.

Example 1

To one liter of water, there were added 80 g of polyvinyl alcohol (degree of polymerization: 1800; degree of saponification 88%), 2 g of meat extract, 6 g of peptone, 2 g of sodium chloride, 2 g of dipotassium hydrogenphosphate and 10 mg of 2,3,5-triphenyl tetrazolium chloride, followed by dissolution thereof with heating, converting the resulting solution into a film by drying it on a polyester film having a thickness of 20 $\mu$m and a size of 1×1 m to give a polyvinyl alcohol film. The polyvinyl alcohol film was bonded to a nylon melt-blown nonwoven fabric (90 g/m$^2$, which had been immersed in a 1% by weight aqueous solution of peptone and then wrung out the solution therefrom, and dried. The resulting laminate was cut into pieces of 45 mm square, followed by adhesion of the piece to a polyester film having a thickness of 100 $\mu$m and a size of 70×80mm and sterilization of the resulting film with ethylene oxide gas to thus give a culture medium.

Figure 4:
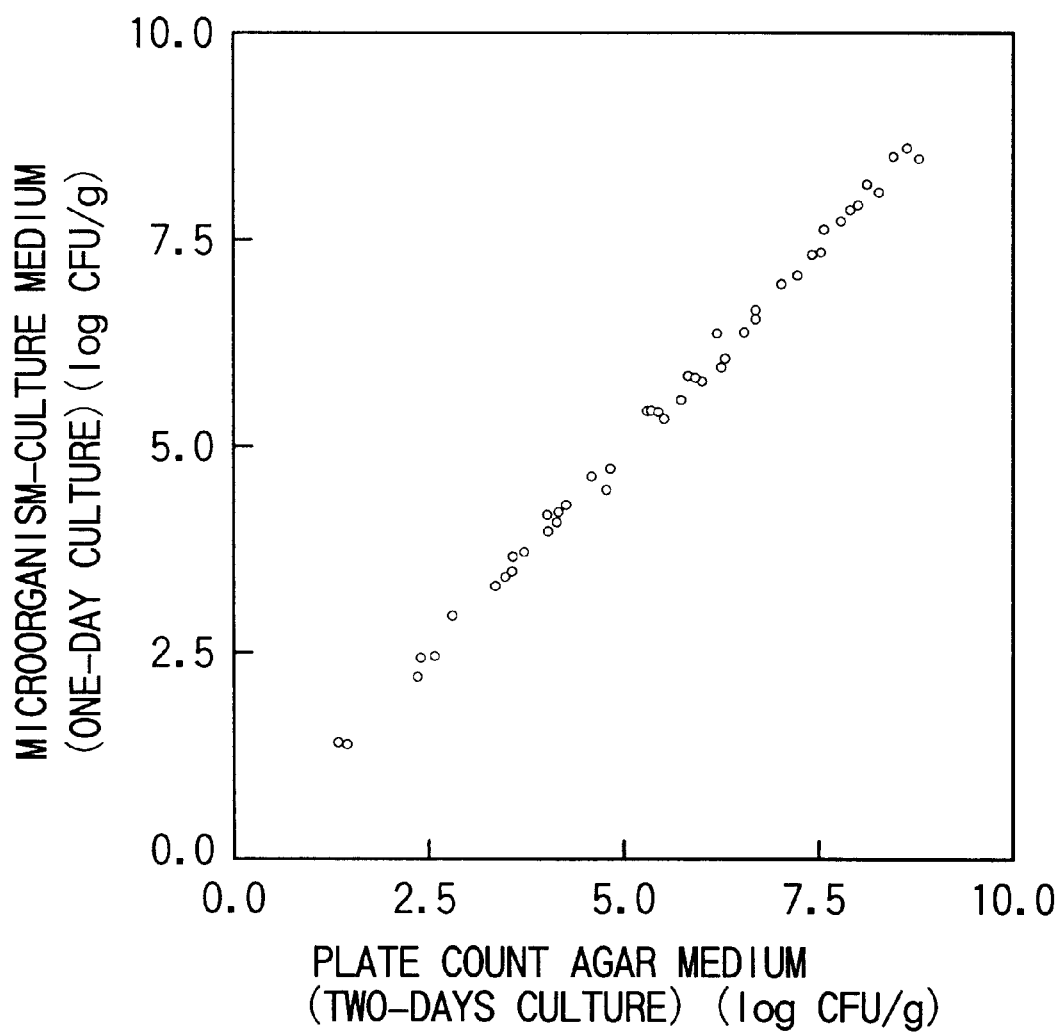
FIG. 4 is a graph showing the relation between the total viable counts on the culture medium of Example 1 and on the plate count agar medium.

Then, a variety of foods such as meat, cut vegetables and household dishes (10 g each) were put in sterilized bags, followed by addition of 100 ml of sterilized water and homogenization using a stomacher. A series of 10-fold diluted liquids were prepared from each sample using sterilized water, followed by adding 1 ml of the diluted liquid to the culture medium prepared above, covering the medium with a polypropylene film having a thickness of 0.04 mm and culturing at 35° C. for 24 hours. At the same time, there was added, to a sterilized Petri dish, 1 ml of another diluted liquid, followed by addition of a plate count agar medium which had been sterilized and maintained at 45° C. to carry out pour culture, culturing at 35° C. for 48 hours and then determination of total viable counts and comparison of the results thus obtained. The total viable counts observed for the culture medium of the present invention and the plate count agar medium show good correlation therebetween as shown in FIG. 4.

Example 2

To one liter of water, there were added 90 g of polyvinyl alcohol (degree of polymerization: 2000; degree of saponification 80%), 8.5 g of peptone, 1.5 g of soybean peptone, 2.5 g of sodium chloride, 1.25 g of dextrose and 1.25 g of dipotassium hydrogenphosphate, followed by dissolution thereof with heating, addition of and mixing of 1 ml of a 1% by weight solution of 2,3,5-triphenyl tetrazolium chloride in ethanol, overlaying the resulting solution on a polyester film having a thickness of 20 $\mu$m and a size of 1×1 m and then drying to thus convert the solution into a film. Then the polyvinyl alcohol film was overlaid on a hydrophilized polyethylene-polypropylene mixed nonwoven fabric (80 g/m$^2$) impregnated with water, followed by drying, cutting the laminate into pieces of 45 mm square, adhesion of the piece to a polyester film having a thickness of 0.1 mm and a size of 60 mm square at the center thereof and sterilization with ethylene oxide gas to thus give a culture medium. Sterilized water (1 ml) was added to the culture medium to thus permeate the water into the culture material. After the culture material was brought into contact with subjects to be tested such as hands or fingers, the culture material was covered with a polypropylene film having a thickness of 0.05 mm, followed by culturing at 35° C. for 24 hours. The area on which microorganisms grew was colored red.

Example 3

A subject to be tested (such as a chopping board, a working table or floor) was wiped up with a sterilized swab over an area of 100 cm$^2$, followed by suspending the microorganisms thus wiped up in 2 ml of sterilized water, preparation of a series of 10-fold diluted liquids from the suspension, addition of 1 ml of the diluted liquid to a culture medium prepared according to the procedures used in Example 2, covering the medium with a polyethylene film having a thickness of 0.08 mm and culturing of the microorganisms at 35° C. for 24 hours. At the same time, there was added, to a sterilized Petri dish, 1 ml of another diluted liquid, followed by addition of a plate count agar medium which had been sterilized and maintained at 45° C. to carry out pour culture, culturing at 35° C. for 48 hours and then determination of total viable counts and comparison of the results thus obtained. The total viable counts observed for the culture medium of the present invention and the plate count agar medium show good correlation therebetween as in Example 1.

Example 4

To 1.5 liter of water, there were added 75 g of polyvinyl alcohol (degree of polymerization: 3000; degree of saponification 88%), 0.5 g of sodium deoxycholate, 5 g of peptone, 1 g of ammonium iron citrate, 2.5 g of sodium chloride, 1 g of dipotassium hydrogenphosphate, 5 g of lactose and 0.0165 9 of Neutral Red, followed by dissolution thereof with heating, converting the resulting solution into a film by drying it on a polyester film having a thickness of 20 μm and a size of 1×1 m to give a polyvinyl alcohol film. The polyvinyl alcohol film was bonded to a rayon nonwoven fabric (80 g/m$^2$, which had been immersed in water and then wrung out the solution therefrom, and dried. The resulting laminate was cut into circular pieces having a diameter of 50 mm, followed by adhesion of the piece to polyethylene-coated paper having a size of 70×80 mm and sterilization of the paper with ethylene oxide gas to thus give a culture medium for culturing the coliforms.

Figure 5:
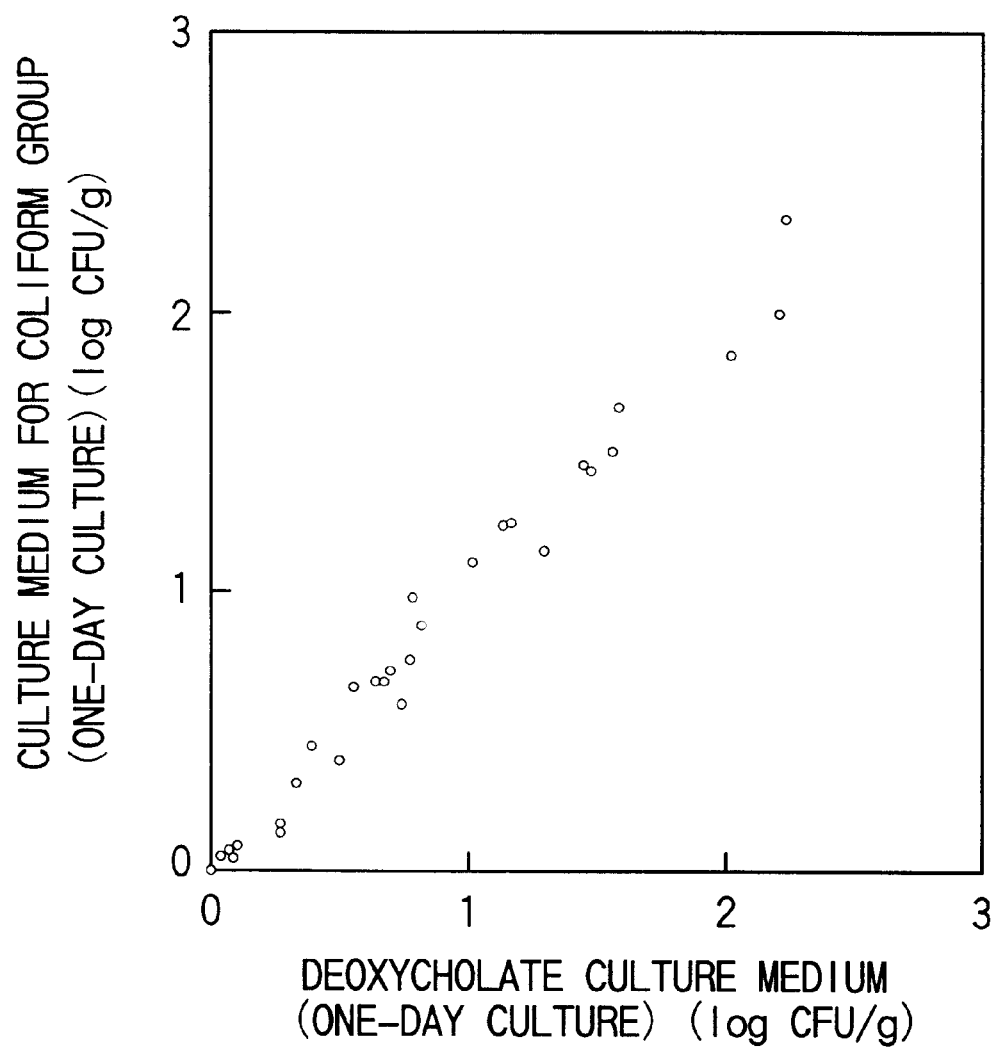
FIG. 5 is a graph showing the relation between the numbers of the coliforms grown on the culture medium of Example 4 and on a deoxycholate medium.

Then, a variety of foods such as meat, cut vegetables and household dishes (10 g each) were put in sterilized bags, followed by addition of 100 ml of sterilized water and homogenization thereof using a stomacher. A series of 10-fold diluted liquids were prepared from each sample using sterilized water, followed by adding 1 ml of the diluted liquid to the culture medium for culturing the coliforms, covering the medium with a polypropylene film having a thickness of 0.04 mm and culturing at 37° C. for 24 hours. At the same time, there was added, to a sterilized Petri dish, 1 ml of another diluted liquid, followed by addition of a deoxycholate medium which had been sterilized and maintained at 45° C. to carry out pour culture, culturing at 37° C. for 24 hours and then counting the number of red turbid colonies and comparison of the results thus obtained. The number of the coliforms grown on the culture medium of the present invention and on the deoxycholate medium show good correlation therebetween as shown in FIG. 5.

Example 5

To 1.5 liter of water, there were added 85 g of carboxyl-modified polyvinyl alcohol (Aquareserve GP-01 available from Nippon Synthetic Chemical Industry, Co., Ltd.)(see "Kogyo Zairyo (Industrial Materials)", 1994, Vol. 42, pp. 31–35; Japanese Patent Nos. 1,495,223 and 1,633,875), 2.5 g of meat extract, 7.5 g of peptone, 2.5 g of sodium chloride and 2.5 g of dipotassium hydrogenphosphate to give an aqueous suspension, followed by homogenization of the suspension, then drying the suspension in the form of a film so that the weight per unit area of the carboxyl-modified polyvinyl alcohol was 85 g/m$^2$, cutting the film into circular pieces having a diameter of 50 mm to give a microorganism culture medium. The resulting culture medium for microorganisms was subjected to the ethylene oxide gas sterilization.

Figure 6:
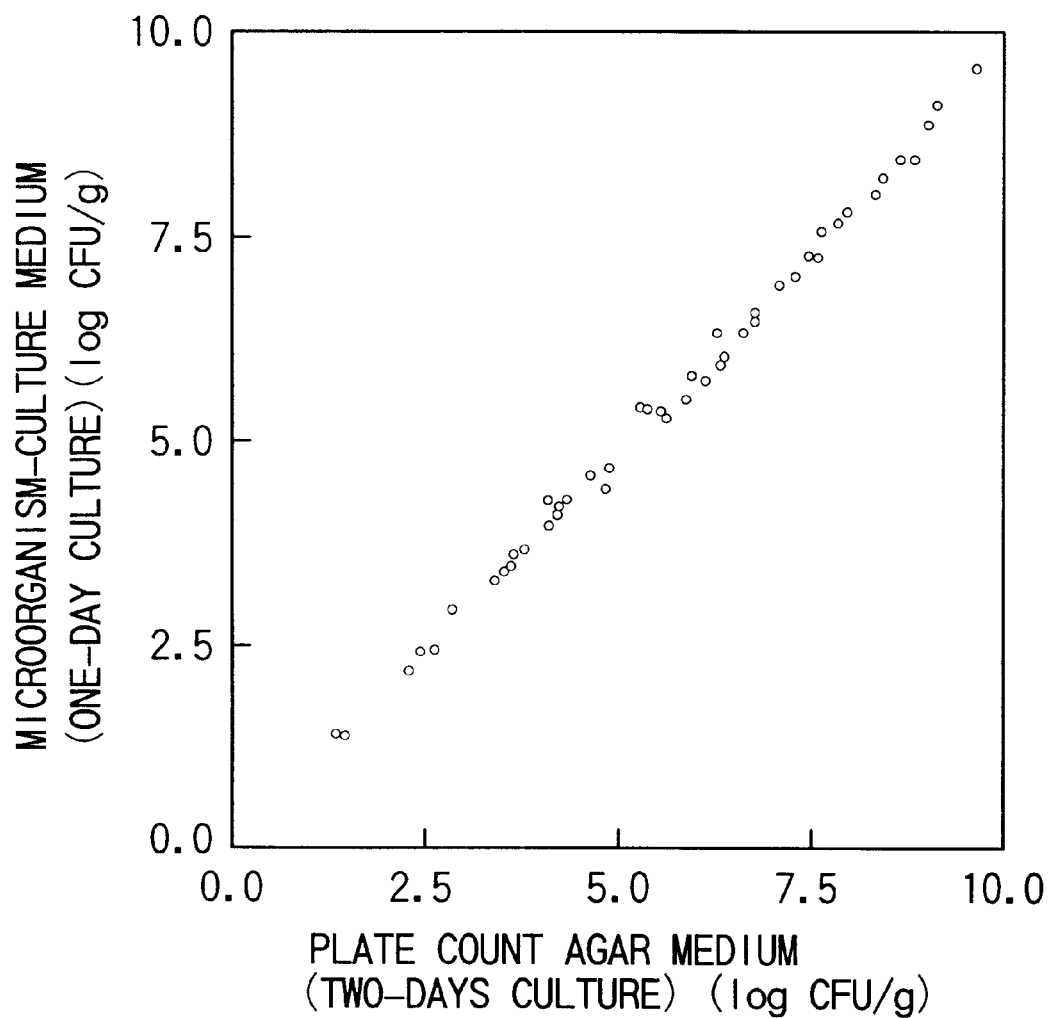
FIG. 6 is a graph showing the relation between the total viable counts on the culture medium of Example 5 and on the plate count agar medium.

Then, a variety of foods such as meat, cut vegetables and household dishes (10 g each) were put in sterilized bags, followed by addition of sterilized water in an amount of 10 times the volume of the food and homogenization using a stomacher. A series of 10-fold diluted liquids were prepared from each sample using sterilized water, followed by adding 1 ml of the diluted liquid to the microorganism culture medium contained in a sterilized Petri dish, covering the medium with a polyethylene film having a thickness of 0.03 mm and culturing at 35° C. for 24 hours to determine the total viable count. At the same time, there was added, to a sterilized Petri dish, 1 ml of another diluted liquid used above, followed by addition of a plate count agar medium which had been sterilized and maintained at 45° C. to carry out pour culture, culturing at 35° C. for 48 hours and then determination of total viable counts and comparison of the results thus obtained. The total viable counts on the culture medium of the present invention and on the plate count agar medium show good correlation therebetween as shown in FIG. 6.

Example 6

To one liter of water, there were added 60 g of polyvinyl alcohol (degree of polymerization: 2400; degree of saponification: 88%), 8.5 g of peptone, 1.5 g of soybean peptone, 2.5 g of sodium chloride, 1.25 g of dextrose and 1.25 g of dipotassium hydrogenphosphate, followed by dissolution thereof with heating. The resulting mixed aqueous solution was overlaid on a polyester film so that the weight per unit area of the polyvinyl alcohol was 60 g/m$^2$, followed by laminating the overlaid film with rayon-polyester mixed nonwoven fabric (80 g/m$^2$), drying and cutting it into pieces having a size of 45 mm square to give a microorganism culture medium, then adhesion of the culture medium to the center of a polyester film having a thickness of 0.1 mm and a size of 60 mm square. The microorganism culture medium was subjected to the ethylene oxide gas sterilization. To the microorganism culture medium, there was added 1 ml of sterilized water, to which 1/1000 volume of a 1% by weight solution of 2,3,5-triphenyl tetrazolium chloride in ethanol had been added, to thus permeate water into the culture medium. After coming the fiber layer side of the culture medium in contact with subjects to be tested such as hands or fingers, the culture medium was covered with a polypropylene film having a thickness of 0.05 mm, followed by culturing at 35° C. for 24 hours. The colonies of the microorganisms were colored red. It was found that the use of this culture medium permitted the formation of colonies on the surface of the fiber layer and that this accordingly made the counting of the colonies easy.

Example 7

To 1.5 liter of water, there were added polyvinyl alcohol (degree of polymerization: 1700; degree of saponification: 88%), starch-acrylic acid-grafted water-absorptive polymer (Sunfresh ST100MPS, available from Sanyo Chemical Industries, Ltd.) meat extract, peptone, sodium chloride and dipotassium hydrogenphosphate (in a ratio (by weight) of 6:2:1:3:1:1), followed by dissolution of these ingredients with heating. A rayon nonwoven fabric (80 g/m$^2$) was impregnated with this aqueous solution to such an extent that the weight per unit area of the polyvinyl alcohol was 75 g/m$^2$, followed by drying and then cutting it into pieces having a size of 45 mm square to give a microorganism culture medium. The microorganism culture medium was subjected to the ethylene oxide gas sterilization. A subject to be tested (such as a chopping board, a working table or floor) was wiped up with a sterilized swab over an area of 100 cm$^2$, followed by suspending the microorganisms thus wiped up in 1 ml of sterilized water, preparation of a series of 10-fold diluted liquids from the suspension, addition of 1 ml of the diluted liquid to a culture medium-containing polyethylene bag having a thickness of 0.04 mm, tightly sealing the bag and culturing at 35° C. for 24 hours. At the same time, there was added, to a sterilized Petri dish, 1 ml of another diluted liquid, followed by addition of a plate count agar medium which had been sterilized and maintained at 45° C. to carry out pour culture, culturing at 35° C. for 48 hours and then determination of the viable counts thereon and comparison of the results thus obtained. The total viable counts on the culture medium of the present invention and on the plate count agar medium show good correlation therebetween as in Example 5.

It was found that the use of this culture medium permitted the formation of colonies on the surface of the fiber layer while maintaining good dispersibility of colonies and that this accordingly made the counting of the colonies easy.

Example 8

The same procedures used in Example 6 were repeated except that a hydrophilized polypropylene nonwoven fabric (70 g/m$^2$) was substituted for the rayon-polyester nonwoven fabric used in Example 6 to give a microorganism culture medium. Tests of hands or fingers were carried out according to the procedures used in Example 6 and results similar to those observed in Example 6 were obtained.

Example 9

Figure 7:
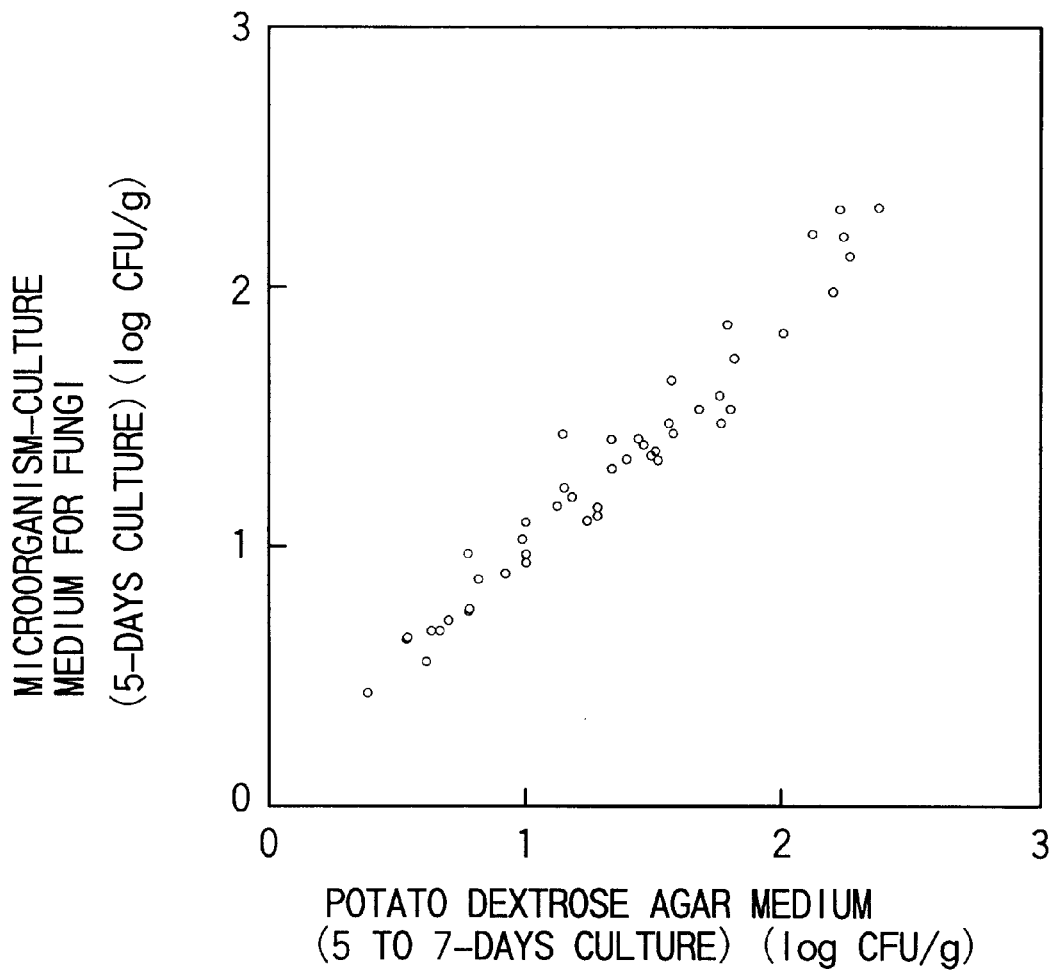
FIG. 7 is a graph showing the relation between the number of yeasts and moulds grown on the culture medium of Example 9 and on a potato dextrose-agar medium.

A water-absorptive polymer sheet D-420 available from Nippon Shokubai Kagaku Kogyo Co., Ltd. (starch-polyacrylic acid composite-crosslinked polymer) was impregnated with an aqueous solution containing 2 g of potato extract and 10 g of dextrose per 1 m$^2$ of the polymer sheet and then dried. The sheet was cut into circular pieces having a diameter of 50 mm, followed by adhesion of the circular piece to the center of polyethylene-coated paper having a thickness of 0.3 mm and a size of 80 mm square to give a microorganism culture medium for use in yeasts and moulds-test. This microorganism culture medium for yeasts and moulds-test was subjected to the ethylene oxide gas sterilization. A subject such as a working table or floor was wiped up with a sterilized swab over an area of 10×20 cm, followed by suspending the microorganisms thus wiped up in 2 ml of sterilized water, preparation of a series of 10-fold diluted liquids from the suspension, addition of 1 ml of the diluted liquid to the microorganism culture medium for yeasts and moulds-test, prepared above, and culturing at 25° C. for 5 days and separately, 0.2 ml of the suspension was applied to a potato dextrose-agar culture medium preliminarily prepared, followed by culturing at 25° C. for 5 to 7 days, determination of total viable counts and comparison of the results thus obtained. The total viable counts on the culture medium of the present invention and on the plate count agar medium show good correlation therebetween as shown in FIG. 7.

Example 10

To one liter of water, there were added 90 g of polyvinyl alcohol (degree of saponification: 88%; degree of polymerization: 1800), 2.4 g of meat extract, 7.2 g of peptone, 2.4 g of sodium chloride, 2.4 g of dipotassium hydrogenphosphate and 10 mg of 2,3,5-triphenyl tetrazolium chloride, followed by dissolution thereof with heating, and forming the resulting solution into a film on a polyester film having a thickness of 20 μm and a size of 1×1 m to thus form a polyvinyl alcohol film. A nylon melt blown nonwoven fabric having a weight per unit area of 95 g/m$^2$, an average fiber diameter of 2.5 μm and a thickness of 1 mm was immersed in a 3% by weight aqueous solution of peptone, followed by squeezing out the solution, bonding of the nonwoven fabric to the foregoing polyvinyl alcohol film, drying and cutting the resulting laminate into circular pieces having a diameter of 50 mm to thus form a microorganism culture medium. The resulting culture medium was adhered to a polyester film having a thickness of 100 μm and a size of 70×80 mm and then subjected to the ethylene oxide gas sterilization.

Figure 8:
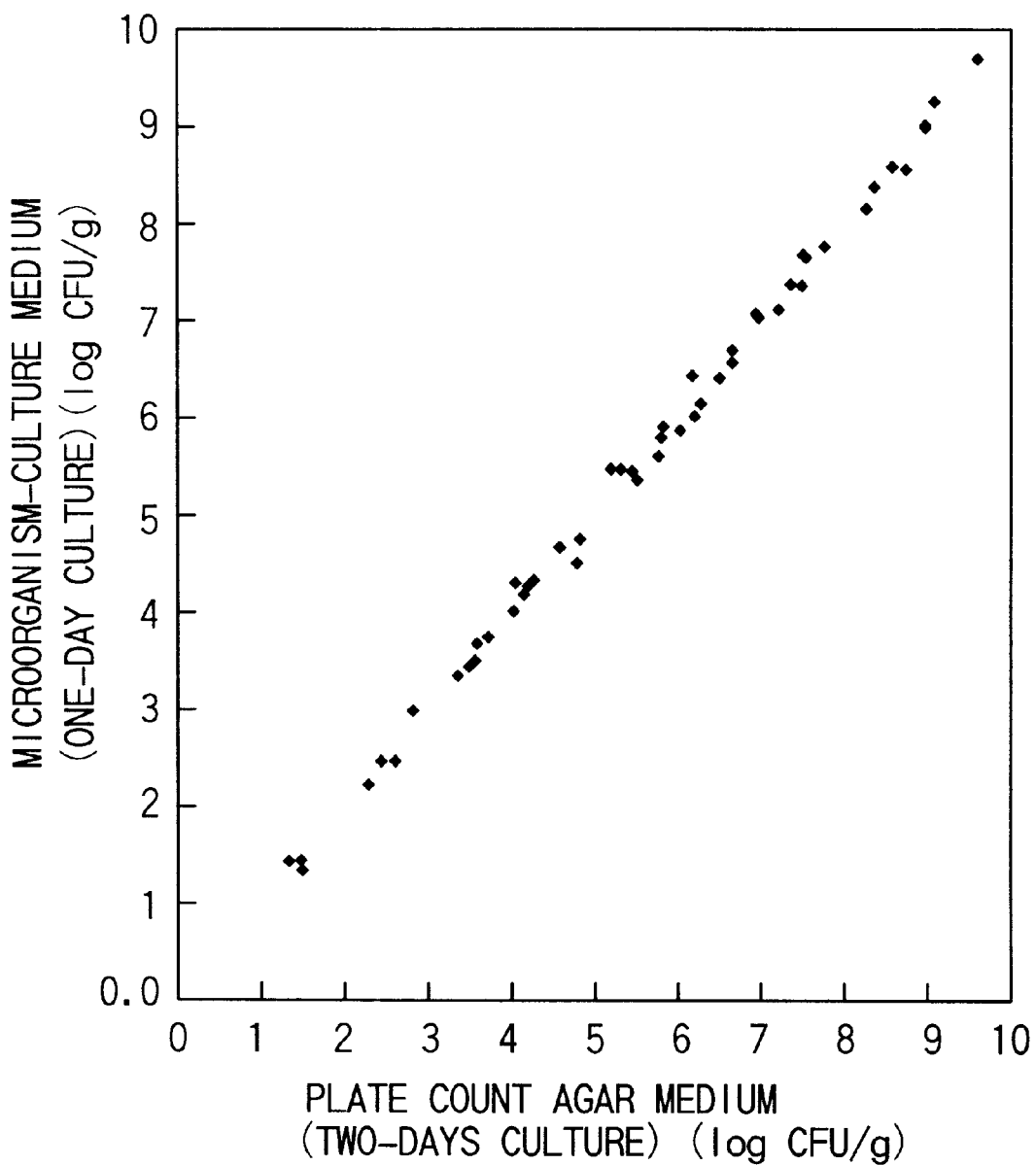
FIG. 8 is a graph showing the relation between the total viable counts on the culture medium of Example 10 and on the plate count agar medium.

Then, a variety of foods such as meat, cut vegetables and household dishes (10 g each) were put in sterilized bags, followed by addition of 100 ml of sterilized water and homogenization using a stomacher. A series of 10-fold diluted liquids were prepared from each sample using sterilized water, followed by adding 1 ml of the diluted liquid to the microorganism culture medium prepared above, covering the medium with a polypropylene film having a thickness of 0.04 mm and culturing at 35° C. for 24 hours. At the same time, there was added, to a sterilized Petri dish, 1 ml of another diluted liquid used above, followed by addition of a plate count agar medium which had been sterilized and maintained at 45° C. to carry out pour culture, culturing at 35° C. for 48 hours and then determination of total viable counts and comparison of the results thus obtained. The total viable counts on the culture medium of the present invention and on the plate count agar medium show good correlation therebetween as shown in FIG. 8.

It was found that the use of this culture medium permitted the formation of colonies on the surface of the fiber layer while maintaining good dispersibility of colonies and that this accordingly made the counting of the colonies easy.

Example 11

A water-absorptive polymer sheet D-420 available from Nippon Shokubal Kagaku Kogyo Co., Ltd. was cut into circular pieces having a diameter of 50 mm and adhered to the center of polyethylene-coated paper having a thickness of 0.3 mm and a size of 80 mm square, followed by the ethylene oxide gas sterilization to thus give a culture material. A solution (1 ml) prepared by dissolving 2 g of potato extract and 10 g of dextrose in one liter of water and then subjecting the solution to autoclave sterilization was added to the resulting culture material, followed by direct wiping up of, for instance, a washed chopping board with the culture material, covering the material with a sterilized polypropylene film having a thickness of 0.04 mm, and culturing at 25° C. There was observed the growth of moulds on about 20% of the culture medium. In other words, it was found that moulds were attached to about 20% of the subjects tested.

Industrial Applicability of the Invention

The culture medium prepared using the culture material of the present invention can be used, by itself, in almost all of the applications such as test of liquid samples, food test, test of environment and direct contact-test and the use of the culture medium also makes the execution of microorganism-test easy. Moreover, the use of the culture medium of the present invention permits the execution of the direct contact-test even if the subject to be tested is curvature and/or more or less uneven. In addition, the culture medium has a small thickness and does not take space when carrying out culturing, and if a supporting sheet is used, the culture medium may more easily be used. Furthermore, the amount of waste generated after the use of the medium can considerably be reduced as compared with the usual microorganism-test. Moreover, when using a microorganism culture material or a microorganism culture medium which comprises a porous matrix layer and a water-soluble polymer layer, it can be used in a test wherein the surface of a subject is directly wiped up with the material or medium and it also permits uniform distribution of colonies on the surface of the culture medium and this in turn makes the counting of colonies easy.

What is claimed is:

1. A microorganism culture material having a water content of not more than 50% by weight and sufficiently insoluble in water such that the culture material substantially holds its original shape for at least 30 minutes when in contact with water having a temperature of not more than 50° C., wherein said culture material comprises a water-soluble polymer layer containing nutrients for growth of a microorganism and a porous matrix layer, said polymer layer and matrix layer being arranged such that when a microorganism and water are applied to the surface of the porous matrix layer the water diffuses through the porous matrix layer to contact and dissolve the water-soluble polymer layer and nutrients therein and the dissolved polymer and nutrients gradually penetrate into the porous matrix layer to unite the polymer and nutrients with the porous matrix layer as single layer, and the microorganism grows on the surface of the matrix layer to form colonies.

2. The microorganism culture material of claim 1, wherein the viscosity of a 4% by weight aqueous solution of the water-soluble polymer at 20° C. ranges from 10 to 80 cps.

3. The microorganism culture material of claim 1, wherein the water-soluble polymer is at least one member selected from the group consisting of polyvinyl alcohol (PVA); modified PVA; cellulose derivatives; starch and derivatives thereof; polysaccharides; acrylic acid and derivatives thereof; polyethers; and proteins.

4. The microorganism culture material of claim 1, wherein the material for forming the porous matrix layer is at least one member selected from the group consisting of textile fabrics, nonwoven fabrics, porous films and sponge materials formed from at least one member selected from the group consisting of synthetic fibers, semi-synthetic fibers, natural fibers and inorganic fibers; and porous ceramics.

5. The microorganism culture material of claim 1 wherein the porous matrix layer has an amount of retained water ranging from 15 to 200 mg/cm$^2$, a weight per unit area ranging from 10 to 200 g/m$^2$ and a density ranging from 3 to 600 kg/m$^3$.

6. The microorganism culture material of claim 1 wherein the water-soluble polymer layer has a weight per unit area equal to 0.5 to 4 times the weight per unit area of the porous matrix layer.

7. The microorganism culture material of claim 1 wherein said material comprises a reinforcing layer.

8. The microorganism culture material according to claim 3, wherein the said polysaccharides is other than the cellulose derivatives and starch and derivatives thereof.

9. A microorganism culture medium produced by adding water to the microorganism culture material as set forth in claim 1 to dissolve the water-soluble polymer layer and nutrients therein so the dissolved polymer and nutrients gradually penetrate into the porous matrix layer to unite the polymer and nutrients with the porous matrix layer as a single layer.

10. A microorganism culture material having a water content of not more than 50% by weight and sufficiently insoluble in water such that the culture material substantially holds its original shape for at least 30 minutes when in contact with water having a temperature of not more than 50° C., wherein said culture material comprises a water-soluble polymer layer and a porous matrix layer, said polymer layer and matrix layer being arranged such that when a microorganism and water containing nutrients for growth of a microorganism are applied to the surface of the porous matrix layer the water diffuses through the porous matrix layer to contact and dissolve the water-soluble polymer layer and the dissolved polymer gradually penetrates into the porous matrix layer to unite the polymer and nutrients with the porous matrix layer as single layer, and the microorganism grows on the surface of the porous matrix layer to form colonies.

11. The microorganism culture material of claim 10, wherein the viscosity of a 4% by weight aqueous solution of the water-soluble polymer at 20° C. ranges from 10 to 80 cps.

12. The microorganism culture material of claim 10, wherein the water-soluble polymer is at least one member selected from the group consisting of polyvinyl alcohol (PVA); modified PVA; cellulose derivatives; starch and derivatives thereof; polysaccharides thereof; acrylic acid and derivatives thereof; polyethers; and proteins.

13. The microorganism culture material of claim 10, wherein the material for forming the porous matrix layer is at least one member selected from the group consisting of textile fabrics, nonwoven fabrics, porous films and sponge-materials formed from at least one member selected from the group consisting of synthetic fibers, semi-synthetic fibers, natural fibers and inorganic fibers; and porous ceramics.

14. The microorganism culture material of claim 10, wherein the porous matrix layer has an amount of retained water ranging from 15 to 200 mg/cm$^2$, a weight per unit area ranging from 10 to 200 g/m$^2$ and a density ranging from 3 to 600 kg/m$^3$.

15. The microorganism culture material of claim 10, wherein the water-soluble polymer layer has a weight per unit area equal to 0.5 to 4 times the weight per unit area of the porous matrix layer.

16. The microorganism culture material of claim 10, wherein said material comprises a reinforcing layer.

17. The microorganism culture material according to claim 12, wherein the said polysaccharides is other than the cellulose derivatives and starch and derivatives thereof.

18. A microorganism culture medium produced by adding water and nutrients to the microorganism culture material as set forth in claim 10 to dissolve the water-soluble polymer layer so that the dissolved polymer gradually penetrates into the porous matrix layer to unite the polymer and nutrients with the porous matrix layer as a single layer.

* * * * *